US010102640B2

United States Patent
Derda et al.

(10) Patent No.: US 10,102,640 B2
(45) Date of Patent: Oct. 16, 2018

(54) REGISTERING THREE-DIMENSIONAL IMAGE DATA OF AN IMAGED OBJECT WITH A SET OF TWO-DIMENSIONAL PROJECTION IMAGES OF THE OBJECT

(71) Applicants: OptiNav Sp. z o.o., Slupsk (PL); OptiMedi Sp. z o.o., Slupsk (PL)

(72) Inventors: Zuzanna Derda, Slupsk (PL); Michal Dyrek, Cracow (PL)

(73) Assignees: OPTINAV SP. Z O.O., Slupsk (PL); OPTIMEDI SP. Z O.O., Slupsk (PL)

(*) Notice: Subject to any disclaimer, the term of this patent is extended or adjusted under 35 U.S.C. 154(b) by 16 days.

(21) Appl. No.: 15/363,965

(22) Filed: Nov. 29, 2016

(65) Prior Publication Data

US 2018/0150960 A1     May 31, 2018

(51) Int. Cl.
*G06K 9/00*     (2006.01)
*G06T 7/33*     (2017.01)
(Continued)

(52) U.S. Cl.
CPC ............ *G06T 7/33* (2017.01); *G06T 7/0012* (2013.01); *G06T 7/11* (2017.01); *G06T 7/73* (2017.01);
(Continued)

(58) Field of Classification Search
CPC ..... G06T 7/33; G06T 7/11; G06T 7/73; G06T 7/0012; G06T 2207/10081;
(Continued)

(56) References Cited

U.S. PATENT DOCUMENTS 5,967,982 A * 10/1999 Barnett .................. A61B 90/10
                                                                 378/206
6,226,548 B1    5/2001 Foley et al.
(Continued)

FOREIGN PATENT DOCUMENTS

EP          2017785 A1      1/2009

OTHER PUBLICATIONS

European Search Report and Written Opinion; dated Mar. 2018; 10 pp.
(Continued)

*Primary Examiner* — Yon Couso
(74) *Attorney, Agent, or Firm* — Harness, Dickey & Pierce, P.L.C.

(57) ABSTRACT

Three-dimensional image data of an imaged object, such as the bone structure of a patient, comprise first and second rigid parts movably connected to each other, in a first state of position and orientation. Sub-regions within the three-dimensional image data are divided into at least first image data and second image data. A set of two-dimensional projection images of the imaged object are taken from first and second different projection directions, while the first and the second rigid parts are in a second state of position and orientation. A processing device registers the first image data with the set of two-dimensional projection images and separately registers the second image data with the set of two-dimensional projection images to obtain first and second registration information, respectively, which is used to determine the position and orientation of the first and second rigid parts in the second state.

19 Claims, 5 Drawing Sheets

(51) Int. Cl.
*G06T 7/00* (2017.01)
*G06T 7/11* (2017.01)
*G06T 7/73* (2017.01)

(52) U.S. Cl.
CPC .............. *G06T 2207/10012* (2013.01); *G06T 2207/10056* (2013.01); *G06T 2207/10081* (2013.01); *G06T 2207/30204* (2013.01)

(58) Field of Classification Search
CPC ...... A61B 2034/2055; A61B 2090/364; A61B 2090/363; A61B 90/361; A61N 5/1049; A61N 5/1039
See application file for complete search history.

(56) References Cited

U.S. PATENT DOCUMENTS

| | | |
|---|---|---|
| 6,348,058 B1 | 2/2002 | Melkent et al. |
| 6,549,645 B1 | 4/2003 | Oikawa et al. |
| 6,560,354 B1 | 5/2003 | Maurer, Jr. et al. |
| 7,260,426 B2 | 8/2007 | Schweikard et al. |
| 7,327,865 B2 | 2/2008 | Fu et al. |
| 7,653,226 B2 | 1/2010 | Gühring et al. |
| 8,831,706 B2 | 9/2014 | Fu et al. |
| 9,119,670 B2 | 9/2015 | Yang et al. |
| 9,241,657 B2 | 1/2016 | Vollmer et al. |
| 2002/0183610 A1 | 12/2002 | Foley et al. |
| 2006/0002630 A1 | 1/2006 | Fu et al. |
| 2008/0095421 A1 | 4/2008 | Sun et al. |
| 2009/0022382 A1 | 1/2009 | Feilkas et al. |
| 2012/0289825 A1 | 11/2012 | Rai et al. |
| 2013/0060146 A1 | 3/2013 | Yang et al. |
| 2013/0079679 A1* | 3/2013 | Roche .................. A61B 5/103 600/594 |
| 2016/0331338 A1 | 11/2016 | West et al. |
| 2017/0165028 A1* | 6/2017 | Hummelink ......... A61B 8/5261 |

OTHER PUBLICATIONS

Austin C. Bourgeois et al.; The evolution of image-guided lumbosacral spine surgery; Jan. 2015; 13 pp.

J.-S. Jarvers et al.; 3D-based navigation in posterior stabilisations of the certical and thioracic spine: problems and Benefits. Results of 451 screws; Apr. 2011; 11 pp.

* cited by examiner

REGISTERING THREE-DIMENSIONAL IMAGE DATA OF AN IMAGED OBJECT WITH A SET OF TWO-DIMENSIONAL PROJECTION IMAGES OF THE OBJECT

FIELD OF THE INVENTION

The invention relates to the registration of three-dimensional image data of an image object, such as a patient. Furthermore, the invention relates to a processing device and an arrangement configured to process image data and to register three-dimensional image data of the imaged object with a set of two-dimensional projection images of the imaged object. The invention can be applied in particular in the field of medical imaging and data fusion and especially in order to prepare and perform medical operations using invasive operation tools. One specific application is image guided navigation of the operation tool, especially in spine surgery.

BACKGROUND OF THE INVENTION

US 2008/0095421 A1 discloses the registration of two-dimensional (2D) X-ray fluoroscopic images with respect to coordinates of three-dimensional (3D) preoperative computed tomography (CT) or magnetic resonance (MR) images of a volume by registering the fluoroscopic images and the 3D images to 3D ultrasound coordinates. The fluoroscopic images are used for real-time monitoring of the medical procedure. The document further describes that the pre-operative CT and/or MR image data may be fused with the intra-operative 2D fluoroscopic images though 2D/3D registration techniques which are generally intensity-based, centerline-based, and landmark-based.

US 2016/0331338 A1 describes non-invasive methods and apparatus for combining 2D angiographic images with 3D scan data for radiosurgical target definition. A plurality of two-dimensional angiographic images with two or more orientations of an angiographic imaging system is acquired, wherein each of the plurality of 2D angiographic images includes a projection of a plurality of non-invasive fiducial markers having a known three-dimensional configuration. A processing device registers selected 2D angiographic images to a 3D scan volume produced by a 3D imaging system. In order to perform the registration, digitally reconstructed radiographs (DRRs) from the 3D scan volume can be generated using the imaging geometry of the two or more orientations of the angiographic imaging system. Selected DRRs are compared to selected 2D angiographic images and a transformation between the 3D scan volume and the 3D object space is found that maximizes a similarity measure between the selected DRRs and the selected angiographic images.

Using preoperative 3D images during surgery has the advantage that the surgeon can rely on images with a higher resolution, and therefore with more detailed image information, compared to X-ray images or other two-dimensional images, which are taken immediately before surgery or during surgery. Furthermore, the preoperative scan may produce image information about tissue that cannot be acquired by the 2D-imaging system.

A specific technical field is spine surgery, but the invention is also applicable with respect to other cases in which the object to be imaged comprises a plurality of rigid parts (for example bones) which are movably connected to each other, in most cases pairwise movable connected to each other. Preoperative image data on one hand and 2D image data taken immediately before or during treatment of the object on the other hand represent the plurality of rigid parts in different states of position and orientation relative to each other. For example two neighboring vertebras of the spine change their relative position and relative orientation when the patient moves. Therefore, the three-dimensional preoperative image data can only be used by the surgeon or technician for treatment (operation) if these limitations are observed.

SUMMARY OF THE INVENTION

According to a basic idea of the present invention, three-dimensional image data of an imaged object that comprises at least a first rigid part and a second rigid part which are movable connected to each other are used for registration with a set of two-dimensional projection images of the imaged object, wherein the set of two-dimensional projection images comprises at least one image taken in a first projection direction and at least one image taken in a second projection direction, the first and second projection directions being different projection directions. The three-dimensional image data represent a region of the imaged object containing the first rigid part and the second rigid part while the first and second rigid parts are in a first state of position and orientation relative to each other. The set of two-dimensional projection images represents a region of the imaged object containing the first rigid part and the second rigid part while the first and the second rigid parts are in a second state of position and orientation relative to each other. Sub-regions corresponding to the first and second rigid parts within the three-dimensional image data are identified and the three-dimensional image data is divided into at least first image data of a first sub-region representing the first rigid part and second image data of a second sub-region representing the second rigid part. The division may be a physical division, i.e. different data sets may be generated, or the division may be a logical division, i.e. the first image data define the first sub-region representing the first rigid part within the whole three-dimensional image data and the second image data define the second sub-region representing the second rigid part within the whole three-dimensional image data. The first image data of the first sub-region are registered with the set of two-dimensional projection images thereby obtaining first registration information, and the second image data of the second sub-region are separately (i.e. independently) registered with the set of two-dimensional projection images thereby obtaining second registration information. Registration in this context means, that each location within the first or second image data is unambiguously assigned to a corresponding location of the set of two-dimensional projection images. For example, a transformation matrix can be obtained as the registration information in each case for the first and second image data. The transformation matrix or an inverted matrix can be used to transform the coordinate system of the first or second image data into the coordinate system of the set of two-dimensional projection images or vice versa. Using the first and second registration information, the position and orientation of the first and the second rigid parts relative to each other according to the second state are determined.

In particular, an articular model of the imaged object can be generated that represents the first rigid part and second rigid part in the determined position and orientation of the first and second rigid parts relative to each other according to the second state. The articular model comprises the three-dimensional image data with respect to the first and second rigid parts and their relative position and orientation.

The invention is not restricted to two rigid parts which are movably connected to each other. The invention can be applied to any number of rigid parts which are connected to each other, in particular pairwise connected to each other in a chain-like configuration. Each rigid part of the configuration which is of interest for the intended treatment of the imaged object is identified by identifying the respective sub-region corresponding to this rigid part within the three-dimensional image data, the three-dimensional image data are divided correspondingly into image data of the respective sub-region and these image data are registered separately from other image data relating to other rigid parts with the set of two-dimensional projection images, thereby obtaining registration information for this particular rigid part. The articular model can therefore contain the three-dimensional image information about several rigid parts and the information about the position and orientation of all of the rigid parts relative to each other.

According to a first aspect of the invention, a method comprises receiving three-dimensional image data of an imaged object that comprises at least a first rigid part and a second rigid part, wherein the first and the second rigid parts are movably connected to each other, wherein the three-dimensional image data represent a region of the imaged object containing the first rigid part and the second rigid part while the first and the second rigid parts are in a first state of position and orientation relative to each other, identifying sub-regions corresponding to the first and second rigid parts within the three-dimensional image data and dividing the three-dimensional image data into at least first image data of a first sub-region representing the first rigid part and second image data of a second sub-region representing the second rigid part, receiving a set of two-dimensional projection images of the image object, wherein the set of two-dimensional projection images comprises at least one image taken in a first projection direction and at least one image taken in a second projection direction, the first and second projection directions being different projection directions, wherein the set of two-dimensional projection images represents a region of the imaged object containing the first rigid part and the second rigid part while the first and the second rigid parts are in a second state of position and orientation relative to each other, by using a processing device, registering the first image data of the first sub-region with the set of two-dimensional projection images thereby obtaining first registration information, separately registering the second image data of the second sub-region with the set of two-dimensional projection images thereby obtaining second registration information, and determining the position and orientation of the first and second rigid parts relative to each other according to the second state using the first and the second registration information.

According to a second aspect a processing device comprises a first port configured to receive three-dimensional image data of an imaged object that comprises at least a first rigid part and a second rigid part, wherein the first and the second rigid parts are movably connected to each other, wherein the three-dimensional image data represent a region of the imaged object containing the first rigid part and the second rigid part while the first and the second rigid parts are in a first state of position and orientation relative to each other, the processing device comprising a processing unit that is configured to identify sub-regions corresponding to the first and second rigid parts within the three-dimensional image data and dividing the three-dimensional image data into at least first image data of a first sub-region representing the first rigid part and second image data of a second sub-region representing the second rigid part, comprising a second port configured to receive a set of two-dimensional projection images of the image object, wherein the set of two-dimensional projection images comprises at least one image taken in a first projection direction and at least one image taken in a second projection direction, the first and second projection directions being different projection directions, wherein the set of two-dimensional projection images represents a region of the imaged object containing the first rigid part and the second rigid part while the first and the second rigid parts are in a second state of position and orientation relative to each other, the processing unit being configured to register the first image data of the first sub-region with the set of two-dimensional projection images thereby obtaining first registration information, to separately register the second image data of the second sub-region with the set of two-dimensional projection images thereby obtaining second registration information, and to determine the position and orientation of the first and second rigid parts relative to each other according to the second state using the first and the second registration information.

According to a third aspect, an arrangement comprises a processing device having a first port configured to receive three-dimensional image data of an imaged object that comprises at least a first rigid part and a second rigid part, wherein the first and the second rigid parts are movably connected to each other, wherein the three-dimensional image data represent a region of the imaged object containing the first rigid part and the second rigid part while the first and the second rigid parts are in a first state of position and orientation relative to each other, the processing device comprising a processing unit that is configured to identify sub-regions corresponding to the first and second rigid parts within the three-dimensional image data and dividing the three-dimensional image data into at least first image data of a first sub-region representing the first rigid part and second image data of a second sub-region representing the second rigid part, the arrangement comprising an imaging device configured to acquire a set of two-dimensional projection images of the image object, wherein the set of two-dimensional projection images comprises at least one image taken in a first projection direction and at least one image taken in a second projection direction, the first and second projection directions being different projection directions, wherein the set of two-dimensional projection images represents a region of the imaged object containing the first rigid part and the second rigid part while the first and the second rigid parts are in a second state of position and orientation relative to each other. The processing unit is configured to register the first image data of the first sub-region with the set of two-dimensional projection images thereby obtaining first registration information, to separately register the second image data of the second sub-region with the set of two-dimensional projection images thereby obtaining second registration information, and to determine the position and orientation of the first and second rigid parts relative to each other according to the second state using the first and the second registration information.

There are different ways of using the registration information obtained with respect to the different rigid parts. A preferred way is to interact with the imaged object and/or to manipulate image data of the imaged object by using the articular model mentioned before. Another preferred way which can be combined with the way mentioned before relates to the acquisition or use of the three-dimensional image data as image data representing a three-dimensional volume of a patient as the imaged object. The three-dimensional volume comprises the region that contains the first rigid part and the second rigid part while the first and the second rigid parts are in the first state of position and orientation relative to each other. Preferably, at least extracts from the first image data of the first sub-region and from the second image data of a second sub-region are displayed correspondingly to the determined position and orientation of the first and second rigid parts and are overlaid to an image of the three-dimensional volume of the patient produced by a surgical microscope. The image produced by the surgical microscope may be a 2D image of the whole three-dimensional volume or of a part of the three-dimensional volume.

As mentioned above with respect to prior art, the set of two-dimensional projection images is preferably acquired after acquiring the three-dimensional image data and after the patient has been positioned and prepared for a medical operation.

A further preferred application relates to tracking a movement of an operation tool relative to the patient using a tracking system. In this case, a coordinate system of the tracking system is registered with the first image data of the first sub-region and with the second image data of the second sub-region. In particular, the registration can be performed using the articular model.

In particular, a representation of the operation tool, of the first image data of the first sub-region and of the second image data of the second sub-region can be displayed as a common image of the three-dimensional volume of the patient correspondingly to the determined position and orientation of the first and second rigid parts relative to each other according to the second state, wherein the representation of the operation tool is displayed in a position and/or orientation with respect to the three-dimensional volume of the patient as determined by the tracking system. Using the registration information, the information about the position and/or orientation of the first and second rigid parts relative to each other and/or using the articular model in connection with a tracking system can be performed in addition to the above-mentioned use.

A reference object may firmly be attached to the patient and the reference object may be observed by the tracking system. Furthermore, information from the tracking system about a position and/or orientation of the operation tool relative to the reference object may be used to register the coordinate system of the tracking system with the first image data of the first sub-region and with the second image data of the second sub-region. The reference object can help at least in some situations to improve the registration of the coordinate system of the tracking system with the first image data and the second image data. Again, the articular model can be used in order to register with the first and second image data.

At least three fiducial markers can be fixed to the object to be imaged, in particular to the surface of the object, and the three-dimensional image data can be acquired while the fiducial markers are fixed to the object. Preferably, the fiducial markers stay fixed to the imaged object at least until the set of two-dimensional projection images is acquired. In this case, but also if the fiducial markers are re-fitted to the object, the set of two-dimensional projection images can also represent the fiducial markers. In particular the fiducial markers can be identified manually and/or automatically in the three-dimensional image data as well as in the set of two-dimensional projection images. During registration of the 3D image data with the set of two-dimensional projection images, the representations of each of the fiducial markers or of the combination of the fiducial markers may be registered to each other in the same manner as the representations of each of the rigid bodies are registered. This takes into account that the relative position and orientation of the fiducial markers on one hand and of the rigid bodies on the other hand, may change. In other words: A coordinate system of the three-dimensional image data can be registered with a coordinate system of the set of two-dimensional projection images by using representations of the at least three fiducial markers in the three-dimensional image data as well as in the set of two-dimensional projection images, when the first image data of the first sub-region is registered with the set of two-dimensional projection images and the second image data of the second sub-region is registered with the set of two-dimensional projection images Alternatively, only set of two-dimensional projection images may represent the at least three fiducial markers.

In any case, the 3D image data and/or the articular model that result(s) from the registration of the 3D image data with the set of two-dimensional projection images preferably represents the at least three fiducial markers. Therefore, the at least three fiducial markers can be used to register the coordinate system of the tracking system with the coordinate system of the 3D image data and/or of the articular model.

The arrangement mentioned above, that comprises the processing device, may also comprise any combination of the following: an operation tool that is usable by a surgeon to operate a patient, a tracking system configured to track a movement of the operation tool relative to the patient, a display in order to display a representation of the operation tool together with the first image data and the second image data, a reference object that is firmly attachable to a patient, a surgical microscope, and/or at least one and preferably three fiducial marker(s) which is/are to be fixed to the imaged object.

The tracking system of the arrangement may be configured to track a movement of the operation tool relative to the patient, wherein the processing unit is configured to register a coordinate system of the tracking system with the first image data of the first sub-region and with the second image data of the second sub-region.

The display of the arrangement may be configured to display on the display a representation of the operation tool, the first image data of the first sub-region and the second image data of the second sub-region as a common image of a three-dimensional volume of the patient correspondingly to the determined position and orientation of the first and second rigid parts relative to each other according to the second state, wherein the representation of the operation tool is displayed in a position and/or orientation with respect to the three-dimensional volume of the patient as determined by the tracking system.

In case of the reference object being part of the arrangement, the tracking system may be configured to observe the reference object and the processing unit may be configured to use information from the tracking system about a position and/or an orientation of the operation tool relative to the reference object to register the coordinate system of the tracking system with the first image data of the first sub-region and with the second image data of the second sub-region.

The surgical microscope of the arrangement may be configured to overlay to a 2D image of the three-dimensional volume of the patient produced by the surgical microscope at least extracts from the first image data of the first sub-region and from the second image data of the second sub-region correspondingly to the determined position and orientation of the first and second rigid parts.

BRIEF DESCRIPTION OF THE DRAWINGS

The present invention will be described in the following by way of example, partially with reference to the attached drawings. The figures of the attached drawings schematically show.

DETAILED DESCRIPTION OF THE PREFERRED EMBODIMENTS

Figure 1:
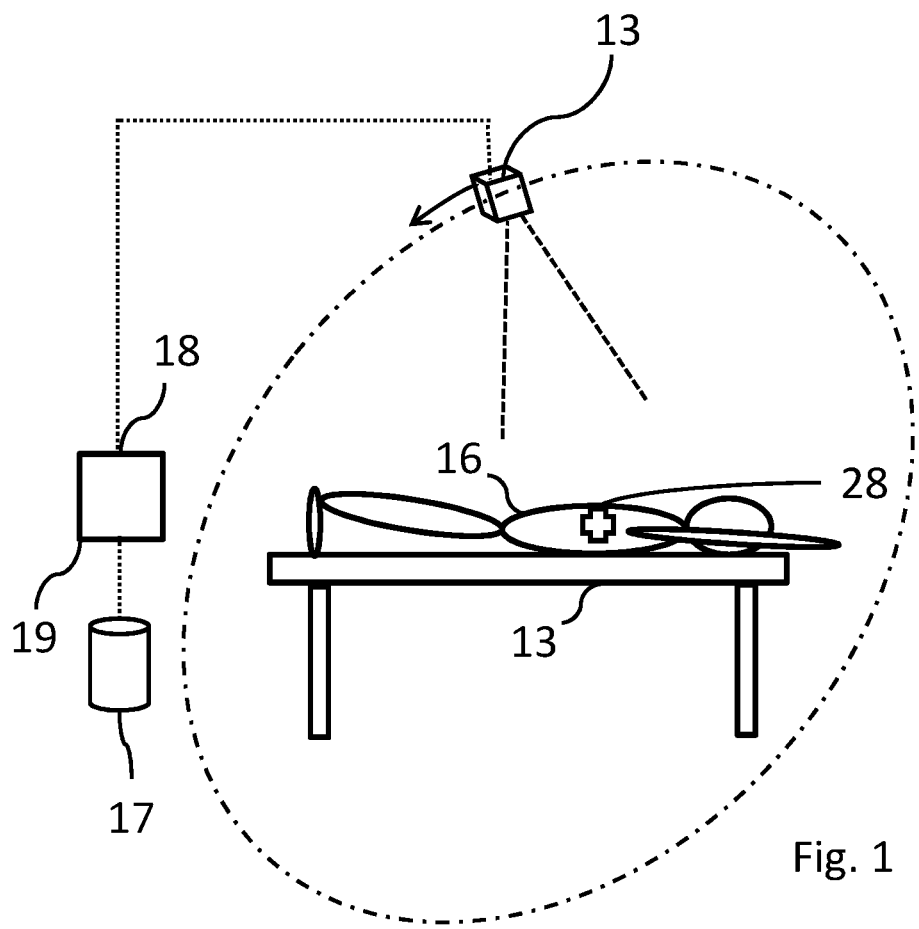
FIG. 1 an arrangement for acquiring three-dimensional image data of a patient while the patient is lying on an examination table, FIG. 2 rigid parts in form of vertebras of the patient's spine, wherein the vertebras are in a first state of position and orientation relative to each other, FIG. 3 the patient of FIG. 1 lying on an operation table while a set of two-dimensional projection images is acquired, FIG. 4 the vertebras of FIG. 2 in a second state of position and orientation relative to each other corresponding to the patient lying on the operation table, FIG. 5 the patient of FIG. 1 and FIG. 3 lying on the operation table while being examined by a surgical microscope, FIG. 6 the patient of FIG. 1 and FIG. 3 lying on the operation table while the patient is examined by the surgical microscope and while a surgical tool is prepared to be used to operate the patient, FIG. 7 an arrangement comprising a processing device, a data storage and a screen as well as a tracking system.

Acquiring 3D image data of a volume at high resolution is time consuming. When 3D image data are acquired pre-operatively, they can be combined later, during operation, with other image data and/or positional information from a tracking system which can be acquired without significant delay. This enables the surgeon or technician to use the pre-operative 3D data combined with information that is continuously updated. Movement of the patient, the operation table or operation chair and/or the surgical tool can be tracked and/or taken into account by the updated information. In particular, the pre-operative 3D images can be displayed on the same screen or other display as the surgical tool while being used during operation. Often, the term "data fusion" is used to express the combination of image data or positional information that stem from different imaging system or tracking systems. The different data and/or information is registered with respect to their coordinate systems so that, for example, the surgical tool can be displayed with the current position and orientation relative to the patient and relative to the pre-operative 3D data and/or the image produced by an optical system, such as a surgical microscope can be augmented by at least extracts from the pre-operative 3D data. Especially in spine surgery, very high precision with respect to the position and orientation of the surgical tool is required and the pre-operative 3D data may be used to increase precision, since they contain a large amount of image information.

The spine and other groups of bones of a human or animal body allow for relative movement of the different bones. Therefore, the movement state generally differs between the situation when the pre-operative 3D image data are acquired and the situation when the patient is operated by the surgeon or team of surgeons. According to the invention, the different rigid parts, in particular bones, which are relevant to the operation are identified within the 3D image data and the corresponding sub-regions each comprising at least one of the rigid parts (bones) are registered separately with the image data taken immediately before the operation and/or during the operation, usually a set of 2D projection images. The registrations can be performed when the patient has been prepared and positioned for the operation. If the patient is not moved or does not move after the acquisition of the set of 2D projection images or other images, the registrations stay valid during operation. Therefore, corresponding information with respect to relative position and orientation of the bones can be used during operation or at least during the operational phase in which the registrations are valid. In the following, the expression "articular model" is used for a set of information comprising the position and orientation of the bones of interest relative to each other. In its simplest form, the articular model consists of image data or extracts from image data allowing the display of all bones of interest in the valid relative position and orientation. In a more elaborate form of the articular model, it comprises the 3D image data for each sub-region of the bones of interest and a transformation matrix for each pair of neighboring bones that allows one of the two neighboring bones of each pair to be transformed with respect to its coordinate system into the coordinate system of the neighboring bone. Other forms of the articular model are possible.

By relying on pre-operative 3D image data, delays due to the acquisition and processing of the 3D data can be avoided during operation. Time consuming 3D data acquisition and 3D reconstruction can be finished before the operation starts. In addition, the irradiation dose can be limited in this manner. A single 3D scan is sufficient. Furthermore, the irradiation dose for the staff, i.e. the surgeons or technicians or medical assistants, is also limited. Technicians or assistants are not required in the operation room in order to perform a 3D scan. Also, the risk of infections can be limited, since 3D scans as well as the acquisition of 2D projection images can be performed before the patient is opened with the first incision. A high precision of data fusion can be achieved, since the 3D data are registered sub-region-wise and, therefore, the position and orientation of the bones precisely matches the current state of position and orientation.

The registration can be performed using fiducials which are inherent to the imaged object/patient. In particular, the characteristic shape of bones can be used for registration, for example by optimizing the mutual information in pairs of images. In any case, DRRs (digitally reconstructed radiographs) can be generated from the 3D image data and the mutual information of many pairs of images can be determined. Each DRR corresponds to a different viewing direction and there is in each case one DRR and one 2D projection image in each pair of images. Optionally, DRRs having the same viewing direction can be used that cover projection volumes of different sizes. The image pair with the highest amount of mutual information corresponds to the point of view relative to the respective sub-region of the 3D image data which matches best to the point of view of the 2D projection image.

The registrations may be performed as semi-automatic procedures. A physician or technician may identify the bones of interest and, if present, at least one fiducial marker or inherent fiducial represented by the 3D image data and/or represented by the 2D image data. Reliability of the registrations may be increased in this manner and time required for the registrations may be reduced. However, it is also possible to perform identifications in a fully automatic manner.

Although not preferred, acquisition of 3D image data during operation can be performed and registrations can be performed during operation for the first time or in addition to registrations before the operation.

Preferred is to use the pre-operative registration results in combination with the tracking of at least one operation tool, in particular a surgical tool. This requires a registration of the coordinate system of the tracking system with the coordinate system of the articular model or the corresponding 3D image information. In this case, the surgeon or technician can observe the at least one operation tool within the coordinate system of the 3D image data when the images are fused and displayed on the same screen or other display (e.g. head-mounted display) or if a view of the technician or surgeon onto the patient or onto a current image of the patient is augmented with at least an extract from the 3D image data.

In the following, an example is described with reference to the attached drawings. In FIG. 1, a patient 16 is shown, lying on an examination table 13. At least one fiducial marker 28 stays fixed to the patient's skin while a scan of the patient 16 is performed in order to obtain 3D image data. FIG. 1 schematically shows an imaging device 13 which receives intrusive radiation representing at least one volume of interest of the patient 16. The imaging device 13 can be moved around the patient 16 as schematically indicated by an oval broken line. For example, the imaging device 13 and optionally further imaging devices receive(s) X-ray radiation from a source not shown in FIG. 1. The X-ray radiation penetrates the volume of interests and its intensity is attenuated corresponding to the structure of the volume of interest. In this manner, image information is produced by the imaging device 13 and optionally by at least one further imaging device from different points of view relative to the volume of interest. The images are transferred to a processing device 19 having a port 18 for receiving the images and the processing device 19 computes a tomographic reconstruction of the volume that results in the desired 3D image data of the volume of interest. Alternatively, other ways of acquiring the 3D image data can be performed. For example, an MR (magnetic resonance) imaging system can be used instead of the system described before. The acquired 3D image data are stored in a data storage 17 which is connected to the processing device 19. In particular, the 3D image data are acquired before the operation of a patient 16 starts.

Figure 2:
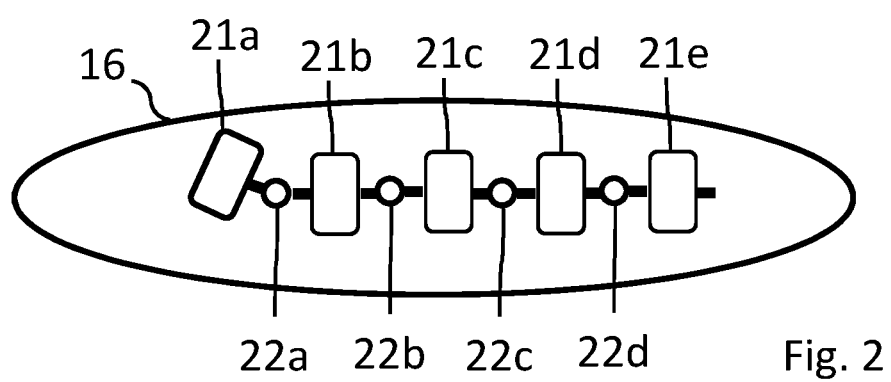

FIG. 2 schematically shows five vertebras 21a, 21b, 21c, 21d, 21e of the patient's spine. The vertebras 21 are pairwise connected to each other via joints 22a, 22b, 22c, 22d. Because of the joints 22; neighboring vertebras 21 can move relative to each other. FIG. 2 shows a first state of position and orientation of the five vertebras 21 relative to each other.

Figure 3:
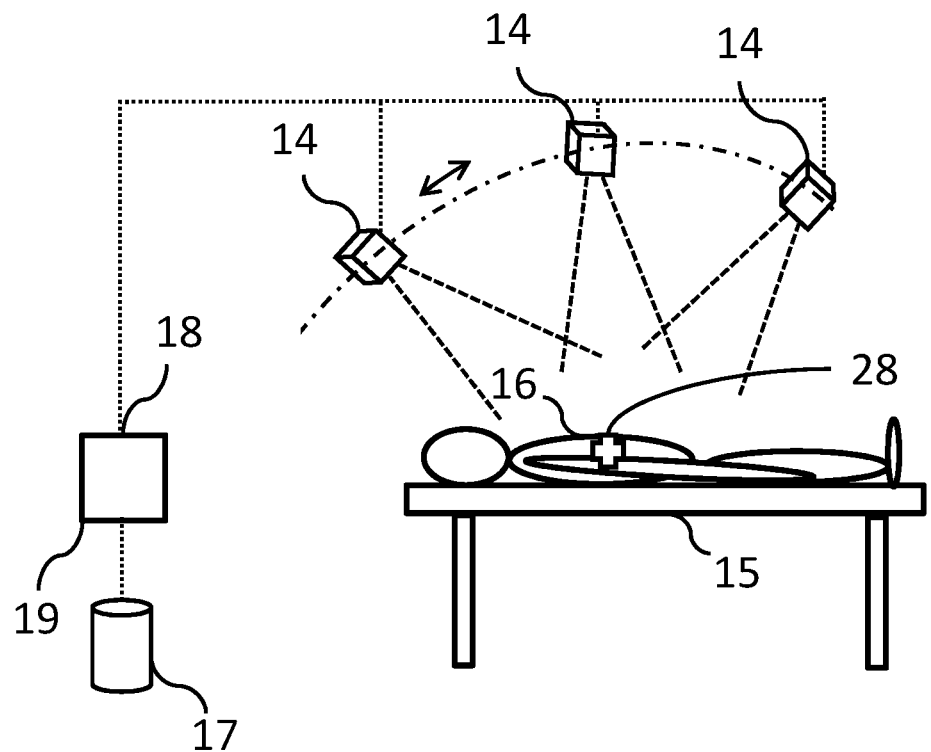

In FIG. 3 the patient 16 is shown lying on an operation table 15. While the patient 16 was examined according to FIG. 1 lying on his/her stomach, the patient 16 is positioned on the operation table 15 lying on his/her back. Preferably, the at least one fiducial marker 28 is still fixed to the patient's skin. In this manner, the current position and orientation of the at least one fiducial marker 28 relative to the rigid bodies, which position and orientation may have changed since the acquisition of the 3D image data, can be captured. At least one imaging device is used to acquire a set of 2D projection images of the volume of interests. In the example described here, the set of projection images capture at least three fiducial markers 28 which are fixed to the patient's skin. This prepares registering the coordinate systems of the 3D image data (or of the articular model) and of the tracking system. It is not necessary, but preferred, that the at least three fiducial markers 28 are also fixed to the patient while the original 3d image data are acquired.

As indicated by an arrow, the at least one imaging device 14 can be moved relative to the patient 16 in order to generate projection images from different points of view. The set of 2D projection images, for example X-ray images, are transferred to a processing device 19 via a port 18 for registration. The processing device 19 may be the same processing device as shown in FIG. 1. Alternatively, the processing device 19 of FIG. 3 may receive the 3D image data from elsewhere, for example from a data storage 17 of the arrangement shown in FIG. 1, for example by data transmission or by using a portable data storage. The processing device 19 of FIG. 3 or the processing device of FIG. 1 identifies the sub-regions of the volume of interest corresponding to the rigid parts, in the example of FIG. 2 and FIG. 4 corresponding to the five vertebras 21. For each vertebra 21, a sub-region of the 3D image data is identified and the 3D image data are divided into five corresponding sub-regions or sets of image data. These sub-regions or sets are separately registered with the set of 2D projection images acquired from the at least one imaging device 14. As a result of the separate registrations, registration information for each of the sub-regions is obtained. Furthermore, the position and orientation of each pair of neighboring rigid parts, in the example of each pair of neighboring vertebras 21, is determined. Optionally, a corresponding articular model is generated.

Figure 4:
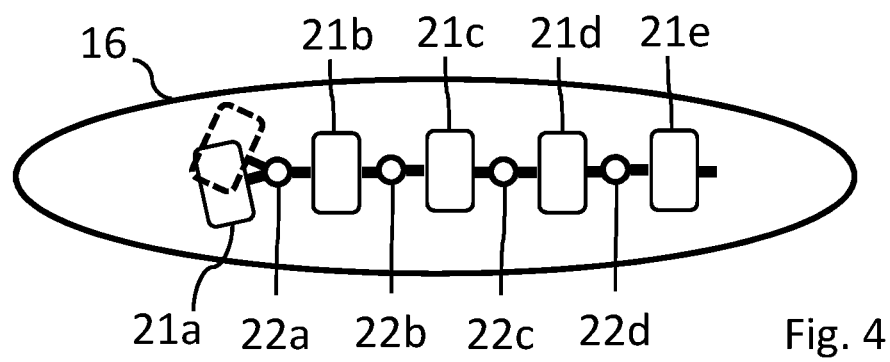

FIG. 4 shows the same volume of interest as FIG. 2, but the vertebras are in a second state of position and orientation relative to each other and the second state differs from the first state shown in FIG. 2. The second state corresponds to the positioning of the patient as shown in FIG. 3. In the specific example, the first vertebra 21a has a different position and orientation compared to the first state shown in FIG. 2. The position and orientation of the first vertebra 21a of FIG. 2 is shown in FIG. 4 using broken lines.

If the patient 16 is moved again or moves again, the at least one imaging device 14 shown in FIG. 3 can be used to acquire a further set of two-dimensional projection images and the registrations are repeated so that updated registration information for each vertebra and the corresponding sub-region in the 3D image data or in the articular module is obtained. This updated information is then used for display of 3D images and/or tracking of operation tool(s).

Figure 5:
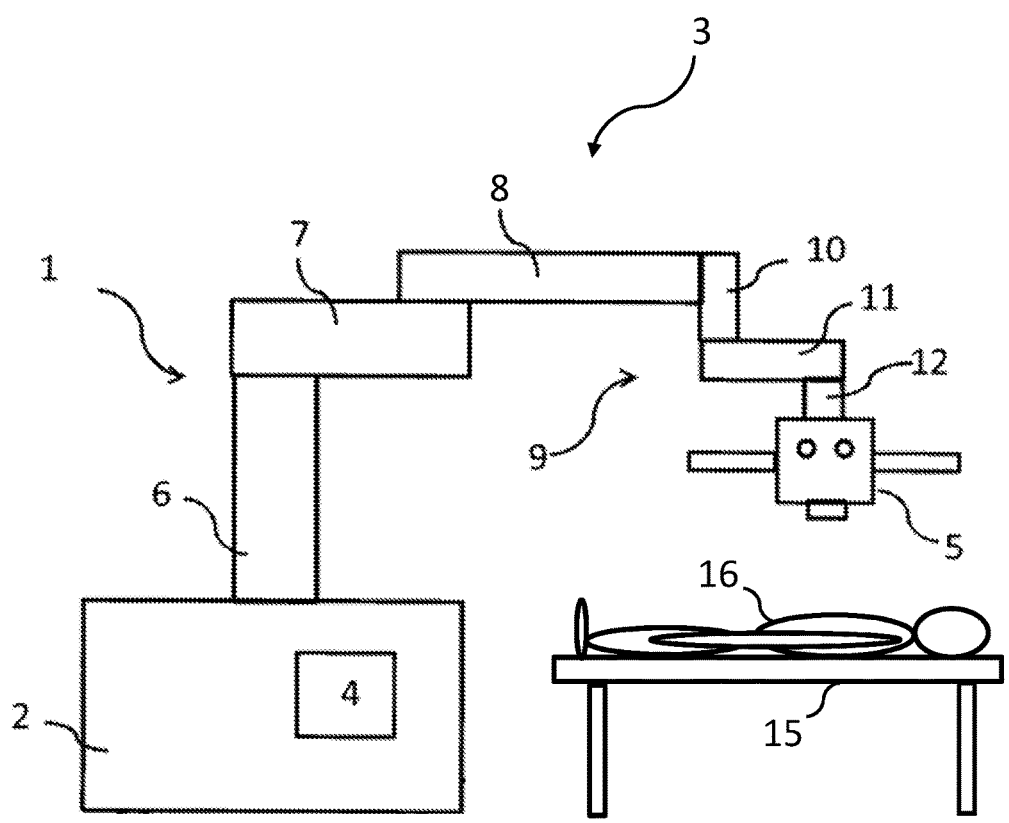

FIG. 5 schematically shows in a simplified manner a surgical microscope and the patient 16 lying on the operation table 15. The surgical microscope 5 can be present at the same time as the at least one imaging device shown in FIG. 3. Alternatively, the imaging device 14 can be removed for the operation and/or the surgical microscope 5 can be positioned further away from the patient 16 while the at least one imaging device(s) 14 acquire(s) projection images. In the latter case, the surgical microscope 5 is moved immediately before the operation starts into a position next to the patient 16.

The surgical microscope system 1 shown in FIG. 5 comprises a base part 2 that rests on the floor or, alternatively, can be moved relative to the floor, for example on wheels. The base part 2 preferably comprises all electronic components for operating the surgical microscope system 1, for example a control device 4 which may be realized as a computer running at least one computer program. In particular, the computer can perform the movement control of the surgical microscope 5 in order to position the optical part (not shown in detail in FIG. 5) of the surgical microscope 5 relative to the patient 16 or relative to the operation table 15. For example, the movement control can be performed so as to keep the optical part in a constant relative position and orientation to the patient 16 when the operation table 15 moves. Optionally, not shown in FIG. 5, a screen and/or another display can be connected to the base part 2. The surgeon or a technician may retrieve information about the operational state, the operation options of the surgical microscope system 1 and/or the images obtained by the surgical microscope 5 from the screen or the other display. Furthermore, the base part 2 may be connected to an interaction device which allows the surgeon or technician to interact with the surgical microscope system 1. For example, the position and/or orientation of the optical part can be controlled by manual interaction. Examples of interaction devices are a keyboard, a joystick, a footswitch and a touchscreen.

The surgical microscope system 1 comprises a carrier 3 in form of a chain of different arms. The carrier 3 comprises a telescope arm 6, a first arm 7 and a second arm 8 and an overhead suspension 9 is attached to the second arm 8. The overhead suspension 9 comprises a connecting part 10, a rotatable arm 11 and a holder 12 which holds the surgical microscope 5. The first arm 7 is rotatable about a rotation axis extending in the longitudinal direction of the telescope arm 6. The second arm 8 is rotatable about a second rotation axis which is parallel to the first rotation axis and extends through the end region of the first arm 7 which neighbors the second arm 8. Therefore, the first arm 7 and the second arm 8 form a joint mechanism which allows the surgical microscope 5 to be moved to a desired position in a plane parallel to the floor of the operation room. Furthermore, the telescope arm 6 allows for movement of the overhead suspension in vertical direction. In addition, the overhead suspension 9 allows for rotational movement of the surgical microscope 5 about three axes of rotation. The first axis of rotation extends in vertical direction and in longitudinal direction of the connecting part 10. The second axis of rotation extends in horizontal direction and in longitudinal direction of the rotatable arm 11. The third axis of rotation extends perpendicularly to the longitudinal axis of the rotatable arm 11, i.e. in the position shown in FIG. 5 extending perpendicularly to the image plane. Movements can be effected by corresponding motors (i.e. linear motors or rotational motors). Corresponding control lines and lines for supplying electric energy to the motors can be integrated in the arms 6, 7, 8 and in the overhead suspension 9.

Figure 6:
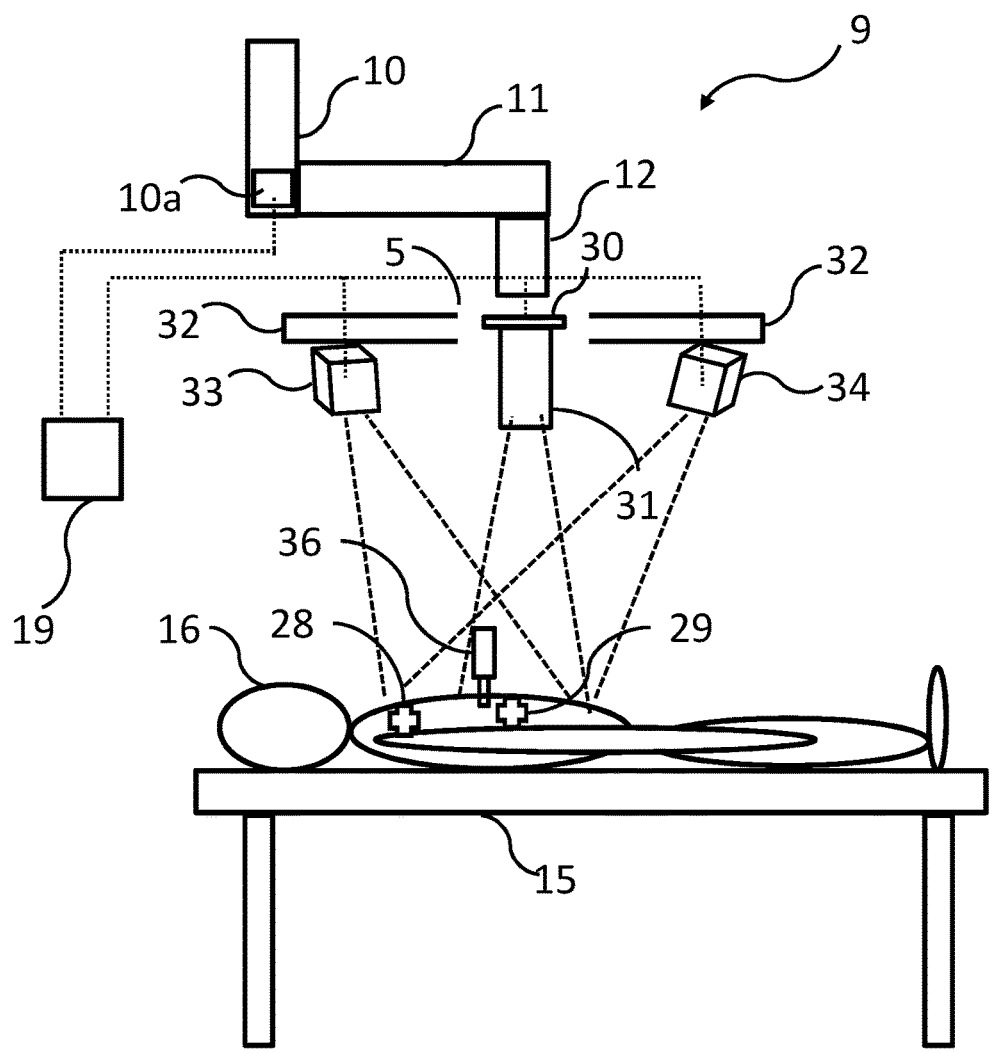

FIG. 6 shows only a part of the surgical microscope system 1, namely the overhead suspension 9, while the patient 16 is lying on the operation table 15. In addition, two cameras 33, 34 of a tracking system are connected to the surgical microscope 5 via arms 32 on opposite sides of the surgical microscope 5. FIG. 6 also schematically shows the optical part 31 and the digital image generator 30 of the surgical microscope 5. In addition, one of the motors 10*a* for effecting movement of the overhead suspension 9 and thereby the surgical microscope 5 is schematically shown in FIG. 6. There is a control line from the motor 10*a* to the processing device 19 which may be the processing device of FIG. 3 that can optionally be integrated in the base part 2 of the surgical microscope system 1 as its control device. The processing device 19 is also connected to the cameras 33, 34 of the tracking system and to the digital image generator 30. During operation of the arrangement, the processing device 19 receives the images from the cameras 33, 34 and evaluates the continuously updated images in order to track the movement of a surgical tool 36 during operation of the patient. The processing device 19 and the cameras 33, 34 form the tracking system. Alternatively, the tracking system may comprise a separate processing device, being a processing device different from the processing device that performs the registrations and optionally displays images visible to the surgeon or technician. Furthermore, the cameras 33, 34 of the tracking system not only capture the surgical tool 36, but also the fiducial markers 28, 29. Either, the fiducial markers 28, 29 are visible to the cameras or additional optical markers (for example circular markers) may be attached to the fiducial markers 28, 29 before the registration of the coordinate system of the tracking system with the coordinate system of the 3D image data and/or of the articular model. The processing device 19 registers the coordinate systems of the tracking system (i.e. the cameras 33, 34) and of the 3D image data, in particular of the articular module. In this process, the fiducial markers 28, 29 or the optional optical markers are used. If one point (e.g. the center point of a spherical fiducial marker region) of each fiducial and/or optical marker 28, 29 is used during registration, at least three markers are required. After registration, the optical markers and the fiducial markers 28, 29 may be removed from the patient. The patient 16 is now prepared for his/her operation. If the registration between the 3D image data and the set of 2D projection images is repeated, for example because the patient has been moved, the registration of the coordinate system of the tracking system with the coordinate system of the 3D image data and/or of the articular model is also repeated, i.e. updated.

The fiducial markers 28, 29 and the optional optical markers are typically located outside of the region which is captured by the surgical microscope 5 and they may also be outside of the region which is captured by the tracking system's cameras 33, 34. The fiducial markers 28, 29 can be removed from the patient before the operation starts. It is preferred that an additional reference body is fixed to at least one of the rigid parts (for example to one of the vertebras) before the operation starts. The reference body is placed within the region which is captured by the tracking system's cameras 33, 34. However, the state of position and orientation of the rigid parts (in particular vertebras) relative to each other must not be changed after the registration of the coordinate systems of the navigation system and of the articular model. During the operation, the tracking system tracks the movement of the operation tool(s) using the representation of the reference body. The surgical tool 36, the cameras 33, 34 of the navigation system and the operation table 16 can be moved during operation. However, if the state of position and orientation of the rigid parts (in particular bones) of interest relative to each other changes during operation, the registration of the 3D image data with the 2D projection images must be updated using a new and currently valid set of 2D projection images. It is preferred that the reference body is positioned closer to the cameras of the navigation system than the surgical tool(s) so that the reference body is always visible to the cameras. The reference body may be any reference body known in the art and is, for example, a body comprising a fixation part for being fixed to the rigid part and a marker holder holding in particular three markers which are visible to the cameras of the tracking system. The markers may be two-dimensional circular areas.

The embodiment shown in FIG. 6 may also comprise a screen and/or another display (e.g. a head-mounted display)

which shows at least one image comprising image information from the 3D image data and further comprising image information from the surgical microscope.

The precision of correctly displaying and/or overlaying 3D images can be verified by pointing with the surgical tool to a known structure (e.g. the reference body and/or one of the rigid parts) while the tool is tracked by the tracking system. It can be verified by viewing the displayed and/or overlaid image if the image correctly shows the surgical tool pointing to the known structure. Instead of the surgical tool, another tool can be used. If the reference body is captured and used by the tracking system, any change in the relative position or orientation of the reference body to the rigid parts also requires new registrations. The same applies if other reference positions (such as anatomical landmarks within the patient and/or fiducial markers on the patient's skin) are used instead of or in addition to the reference body.

It is preferred that the fiducial markers fixed to the patient's skin are not removed at all or are removed only when the reference body is fixed to the rigid part structure or when the other reference positions have been acquired and are available to the tracking system. Leaving the fiducial markers on the patient's skin facilitates the procedure when a new set of 2D projection images needs to be acquired and the registrations need to be updated.

Figure 7:
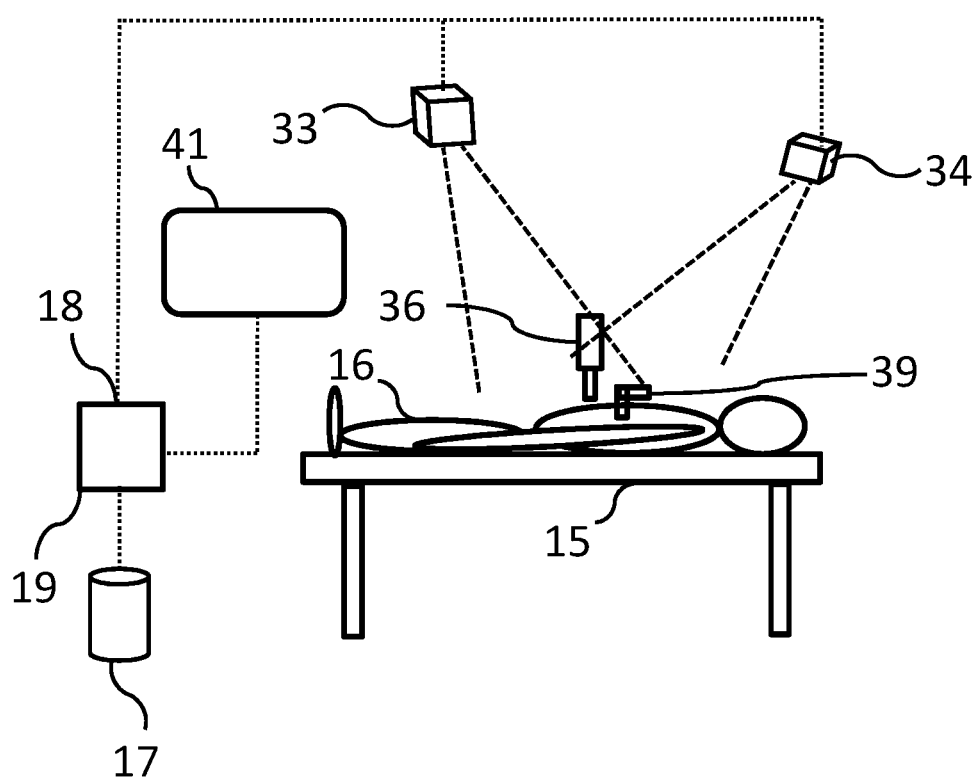

FIG. 7 shows an arrangement similar to the arrangement shown in FIG. 6. However, there is no surgical microscope in the arrangement shown in FIG. 7 and the cameras 33, 34 of the tracking system are therefore not fixed to a surgical microscope. For example, they may be fixed to walls and/or the ceiling of the operation room and/or may be fixed to carriers resting on the floor of the operation room or being fixed to any other part of the operation room. The number of the cameras of the tracking system can differ from two. More cameras increase the information and reduce the risk that the view of a camera onto the operation tool and onto any positional reference is obscured and, therefore, the function of the tracking system is disordered.

In any embodiment, not only the embodiments illustrated by FIG. 6 or FIG. 7, the tracking system can be combined with a device or system for automatically moving at least one surgical tool or other tool during operation. In this manner, the tracking system can be part of an automatic navigation system.

Furthermore, the embodiments illustrated in FIG. 6 and FIG. 7 can be combined. This means that any part which is disclosed as a part of one of the embodiments can also be part of a combined embodiment.

The embodiment shown in FIG. 7 comprises a processing device 19 having a port 18 for receiving the camera signals from the cameras 33, 34 of the tracking system. The processing device 19 may be the processing device of FIG. 3 or not. In any case, the 3D image data and the registration information relating to the registrations of the fixed parts with the set of 2D projection images as well as the registration information relating to the tracking system are stored in a data storage 17 that is connected to the processing device 19. Furthermore, there is a screen 41 and/or another display connected to the processing device 19. During operation, the surgeon and optionally also the technician or assistant can view on the screen at least one image which shows the volume of interest within the patient. This at least one image contains image information from the 3D image data. Furthermore, the at least one image can also comprise a representation of the at least one surgical tool or other tool that is used to interact with the volume of interest. FIG. 7 also shows the reference body 39 which is attached to the structure of rigid parts which also forms at least a region of the volume of interests. Similar to FIG. 6, the surgical tool 36 is also shown.

In the following, an embodiment of registering the 3D image data with the set of 2D projection images is described. In a first, optional step, the positions of fiducial markers and/or of natural markers (e.g. bones) are manually identified within the 3D image data. In a second step, each rigid part of interest is identified in particular by identifying its position within the 3D coordinate system and optionally its name is assigned to the identified rigid part, for example the vertebra name. In a third step the set of 2D projection images is acquired. Preferably, at least two of the projection images which are acquired from the same state of position and orientation are acquired in viewing directions that are perpendicular or nearly perpendicular to each other. This does not exclude that at least a third projection image is taken in a direction that is not perpendicular to other viewing directions. In a fourth optional step, the positions of fiducial markers and/or of natural markers (e.g. bones) are manually identified within the set of 2D projection images. In particular, circular or spherical markers produce elliptic images and the viewing direction as well as the center of the marker can be determined from the elliptic area. In a fifth step, the rigid parts of interests are identified, in particular in a manner corresponding to the second step. In a sixth step, DRRs are generated from the 3D image data. Each DRR corresponds to a point of view and to a viewing direction of the simulated projection and this information is assigned to the DRR. In a seventh step, the best fitting DRRs are identified, i.e. for each of the projection images one DRR is identified which fits best. For example, the criterion for the best fit may be based on the requirement that the mutual information in the respective pair of images is maximal. In an eighth step, the relative positions of markers and rigid parts of interests are identified. In a ninth step, an articular model of the rigid parts of interest and optionally also of the marker positions within the 3D volume is generated. The model contains the information necessary to display 2D cut images of arbitrary cut planes of the rigid parts of interest and of the markers corresponding to the current state of position and orientation.

Generally the registration of the DRRs with the 2D projection images can be performed with so-called local and/or so-called global optimization methods. In case of the identification of a maximum, local optimization delivers a local maximum and global optimization should deliver the global maximum. Preferably, a combination of local and global optimization methods is used. This may increase automation and performance.

It is sufficient to use two 2D projection images, but a larger number of 2D projection images is preferred. According to an example of the registration method to be applied for each rigid part, a library of the DRRs is generated. This means that the same DRR can be used not only once without generating it again. Not only the DRRs themselves but also the corresponding positions of the points of view from which the simulated 2D projection images are acquired are stored within the library. Each DRR in the library is assigned to corresponding position of the point of view. The DRRs are then pair-wise compared to the reference images, i.e. the 2D projection images which have been taken. Any similarity measure that is known in the art can be used to generate a value of mutual information for each pair. In addition, at least one of several optimization algorithms can be applied to find the DRR with the maximum mutual information for each rigid part and for each of the 2D projection images that serve as reference images.

Different optimization algorithms have different ways of converging to a maximum of mutual information and to identify the global maximum of mutual information. For each DRR which fits best to the corresponding reference image, the position of the point of view and (if also stored) the viewing direction is output. Since there are at least two reference images, at least two positions of points of views are identified and this serves as a basis for calculating the transformation matrix which transforms the coordinate system of the sub-region of the 3D image data which contains the respective rigid part with the coordinate system of the set of reference images.

One suitable optimization strategy is the so-called Downhill Simplex algorithm. Another suitable optimization algorithm is global optimization using the Differential Evolution algorithm. Local optimization as applied by Downhill Simplex algorithm converges faster than the global optimization. Global optimization can compensate for larger inaccuracies in the initial position of point of view and the viewing direction. The viewing direction can be eliminated from the optimization procedure if, as preferred, the respective volume of interest of each rigid part is always centered within the image. If any of the optimization algorithms converges to a local maximum which is not the global maximum, this can be recognized by the surgeon or the technician and, in particular, after a shift of the position of the point of view by choosing a corresponding DRR, the algorithm can be restarted.

Preferably, as mentioned before, global and local optimization is combined. In a first stage, global optimization is performed to find a first, initial maximum of mutual information. Then, local optimization is applied which refines the solution by finding the position of maximum mutual information more precisely. With this approach, a fully automatic registration can be performed.

Examples of fiducial markers which can be fixed to the patient's skin are spherical non-metallic circular markers of 3-5 mm in particular 4 mm diameter that are visible to the invasive radiation used for the acquisition of the 3D imaged data. They can be combined with plastic PPSU (Polysulfone) plates that can be fixed to the patient's skin using an adhesive. In particular, there may be a circular hole in the plate center for attaching the plate to the fiducial marker. Especially when radiation in the X-ray range is used both for 3D and 2D projection image acquisition, these plates are visible in both cases.

Alternatively, cylindrical fiducials with a thread in the range from 10 to 15 mm and in particular 12 mm diameter can be used. They can be combined with plastic plates with a corresponding threaded pin in the bottom.

By choosing a plate with a material that is visible to the image acquisition systems or at least one of the acquisition systems, the fiducial markers can be adapted to any imaging system. It is therefore possible to replace the plates when the 3D image data have been acquired so that the replacing plate is visible to the 2D projection imaging system. In addition the plates can be replaced later with plates that are visible to the tracking system, which may be an optical tracking system or a magnetic tracking system.

The reference body may be clamped to a rigid part of the structure of rigid parts of interest. Therefore, the reference body may comprise a clamp, the clamping force of which is preferably adjustable by the surgeon. For example, the clamp may comprise a screw and by turning the screw using a screwdriver the clamping force can be adjusted. Optionally, there are spikes on the surface of the clamp that contact the rigid part. This may help to ensure its secure and stable mounting position on the rigid part, especially on the bone.

When the registrations of the 3D image data and the 2D projection image data have been performed 2D cut images can be produced in any desired cut plane.

The invention claimed is:

1. A method comprising:
    receiving three-dimensional image data of an imaged object that comprises at least a first rigid part and a second rigid part, wherein the first and the second rigid parts are movably connected to each other, wherein the three-dimensional image data represent a region of the imaged object containing the first rigid part and the second rigid part while the first and the second rigid parts are in a first state of position and orientation relative to each other,
    identifying sub-regions corresponding to the first and second rigid parts within the three-dimensional image data and dividing the three-dimensional image data into at least first image data of a first sub-region representing the first rigid part and second image data of a second sub-region representing the second rigid part,
    receiving a set of two-dimensional projection images of the imaged object, wherein the set of two-dimensional projection images comprises at least one image taken in a first projection direction and at least one image taken in a second projection direction, the first and second projection directions being different projection directions, wherein the set of two-dimensional projection images represents a region of the imaged object containing the first rigid part and the second rigid part while the first and the second rigid parts are in a second state of position and orientation relative to each other that is different from the first state, and
    using a processing device, registering the first image data of the first sub-region with the set of two-dimensional projection images thereby obtaining first registration information, separately registering the second image data of the second sub-region with the set of two-dimensional projection images thereby obtaining second registration information, and determining the position and orientation of the first and second rigid parts relative to each other according to the second state using the first and the second registration information.

2. The method of claim 1, further comprising interacting with the imaged object and/or manipulating image data of the imaged object by using an articular model of the imaged object that represents the first rigid part, the second rigid part and the position and orientation of the first and second rigid parts relative to each other.

3. The method of claim 1, further comprising acquiring the three-dimensional image data, wherein the three-dimensional image data are data representing a three-dimensional volume of a patient being the imaged object, the three-dimensional volume comprising the region containing the first rigid part and the second rigid part while the first and the second rigid parts are in the first state of position and orientation relative to each other.

4. The method of claim 3, further comprising acquiring the set of two-dimensional projection images after acquiring the three-dimensional image data, wherein the set of two-dimensional projection images is acquired after the patient has been positioned and prepared for a medical operation.

5. The method of claim 3, the method further comprising tracking a movement of an operation tool relative to the patient using a tracking system, wherein a coordinate system of the tracking system is registered with the first image data of the first sub-region and with the second image data of the second sub-region.

6. The method of claim 5, wherein a representation of the operation tool, the first image data of the first sub-region and the second image data of the second sub-region are displayed as a common image of the three-dimensional volume of the patient correspondingly to the determined position and orientation of the first and second rigid parts relative to each other according to the second state, wherein the representation of the operation tool is displayed in a position and/or orientation with respect to the three-dimensional volume of the patient as determined by the tracking system.

7. The method of claim 5, wherein a reference object is firmly attached to the patient, the reference object is observed by the tracking system and information from the tracking system about a position and/or orientation of the operation tool relative to the reference object is used to register the coordinate system of the tracking system with the first image data of the first sub-region and with the second image data of the second sub-region.

8. The method of claim 3, wherein at least extracts from the first image data of the first sub-region and from the second image data of the second sub-region are displayed correspondingly to the determined position and orientation of the first and second rigid parts and are overlaid to an image of the three-dimensional volume of the patient produced by a surgical microscope.

9. The method of claim 1, wherein the three-dimensional image data also represent at least three fiducial markers which are fixed to the imaged object while the three-dimensional image data are acquired.

10. The method of claim 9, wherein the set of two-dimensional projection images also represents the at least three fiducial markers which are fixed to the imaged object while the set of two-dimensional projection images of the imaged object is acquired,
the method further comprising registering a coordinate system of the three-dimensional image data with a coordinate system of the set of two-dimensional projection images by using representations of the at least three fiducial markers in the three-dimensional image data as well as in the set of two-dimensional projection images, when the first image data of the first sub-region is registered with the set of two-dimensional projection images and the second image data of the second sub-region is registered with the set of two-dimensional projection images.

11. A processing device comprising:
a first port configured to receive three-dimensional image data of an imaged object that comprises at least a first rigid part and a second rigid part, wherein the first and the second rigid parts are movably connected to each other, wherein the three-dimensional image data represent a region of the imaged object containing the first rigid part and the second rigid part while the first and the second rigid parts are in a first state of position and orientation relative to each other,
a processing unit that is configured to identify sub-regions corresponding to the first and second rigid parts within the three-dimensional image data and dividing the three-dimensional image data into at least first image data of a first sub-region representing the first rigid part and second image data of a second sub-region representing the second rigid part, and
a second port configured to receive a set of two-dimensional projection images of the imaged object, wherein the set of two-dimensional projection images comprises at least one image taken in a first projection direction and at least one image taken in a second projection direction, the first and second projection directions being different projection directions, wherein the set of two-dimensional projection images represents a region of the imaged object containing the first rigid part and the second rigid part while the first and the second rigid parts are in a second state of position and orientation relative to each other that is different from the first state,
wherein the processing unit is configured to register the first image data of the first sub-region with the set of two-dimensional projection images thereby obtaining first registration information, to separately register the second image data of the second sub-region with the set of two-dimensional projection images thereby obtaining second registration information, and to determine the position and orientation of the first and second rigid parts relative to each other according to the second state using the first and the second registration information.

12. The processing device of claim 11, wherein the processing unit is further configured to generate an articular model of the imaged object that represents the first rigid part and the second rigid part in the determined position and orientation of the first and second rigid parts relative to each other according to the second state.

13. An arrangement comprising:
a processing device having a first port configured to receive three-dimensional image data of an imaged object that comprises at least a first rigid part and a second rigid part, wherein the first and the second rigid parts are movably connected to each other, wherein the three-dimensional image data represent a region of the imaged object containing the first rigid part and the second rigid part while the first and the second rigid parts are in a first state of position and orientation relative to each other,
wherein the processing device comprises a processing unit that is configured to identify sub-regions corresponding to the first and second rigid parts within the three-dimensional image data and dividing the three-dimensional image data into at least first image data of a first sub-region representing the first rigid part and second image data of a second sub-region representing the second rigid part,
the arrangement further comprising an imaging device configured to acquire a set of two-dimensional projection images of the imaged object, wherein the set of two-dimensional projection images comprises at least one image taken in a first projection direction and at least one image taken in a second projection direction, the first and second projection directions being different projection directions, wherein the set of two-dimensional projection images represents a region of the imaged object containing the first rigid part and the second rigid part while the first and the second rigid parts are in a second state of position and orientation relative to each other that is different from the first state, and further wherein
the processing unit is configured to register the first image data of the first sub-region with the set of two-dimensional projection images thereby obtaining first registration information, to separately register the second image data of the second sub-region with the set of two-dimensional projection images thereby obtaining second registration information, and to determine the position and orientation of the first and second rigid parts relative to each other according to the second state using the first and the second registration information.

14. The arrangement of claim 13, further comprising an operation tool that is usable by a surgeon to operate a patient.

15. The arrangement of claim 14, further comprising a tracking system configured to track a movement of the operation tool relative to the patient, wherein the processing unit is configured to register a coordinate system of the tracking system with the first image data of the first sub-region and with the second image data of the second sub-region.

16. The arrangement of claim 15, further comprising a display configured to display a representation of the operation tool, the first image data of the first sub-region and the second image data of the second sub-region as a common image of a three-dimensional volume of the patient correspondingly to the determined position and orientation of the first and second rigid parts relative to each other according to the second state, wherein the representation of the operation tool is displayed in a position and/or orientation with respect to the three-dimensional volume of the patient as determined by the tracking system.

17. The arrangement of claim 15, further comprising a reference object that is firmly attachable to a patient, wherein the tracking system is configured to observe the reference object and wherein the processing unit is configured to use information from the tracking system about a position and/or an orientation of the operation tool relative to the reference object to register the coordinate system of the tracking system with the first image data of the first sub-region and with the second image data of the second sub-region.

18. The arrangement of claim 13, further comprising a surgical microscope and is configured to overlay to an image of the three-dimensional volume of the patient produced by the surgical microscope at least extracts from the first image data of the first sub-region and from the second image data of the second sub-region correspondingly to the determined position and orientation of the first and second rigid parts.

19. The arrangement of claim 13, further comprising at least three fiducial markers which are fixed to the imaged object while the three-dimensional image data and the set of two-dimensional projection images are acquired.

* * * * *